United States Patent [19]

Miller et al.

[11] Patent Number: 4,654,451

[45] Date of Patent: Mar. 31, 1987

[54] INHIBITING POLYMERIZATION OF VINYL AROMATIC MONOMERS

[75] Inventors: Richard F. Miller, Humble; Marilyn W. Blaschke, Pearland, both of Tex.

[73] Assignee: Atlantic Richfield Company, Los Angeles, Calif.

[21] Appl. No.: 813,805

[22] Filed: Dec. 27, 1985

[51] Int. Cl.4 .................................................. C07C 7/20
[52] U.S. Cl. ................... 585/5; 208/48 AA; 252/403; 252/404; 252/405; 585/435; 585/440; 585/864; 585/866; 585/952
[58] Field of Search .................... 585/2, 3, 4, 5, 435, 585/440, 864, 866, 865, 952; 208/48 AA; 252/403, 404, 405

[56] References Cited

U.S. PATENT DOCUMENTS

| | | | |
|---|---|---|---|
| 2,361,538 | 10/1944 | Franz | 585/3 |
| 2,867,672 | 1/1959 | Hemmerich | 585/4 |
| 3,527,822 | 9/1970 | Benson | 208/48 AA |
| 4,237,326 | 12/1980 | Fuga et al. | 585/4 |

FOREIGN PATENT DOCUMENTS

| | | | |
|---|---|---|---|
| 1064845 | 4/1967 | United Kingdom | 585/5 |
| 2056481 | 3/1981 | United Kingdom | 585/5 |

*Primary Examiner*—Asok Pal
*Attorney, Agent, or Firm*—Coleman R. Reap

[57] ABSTRACT

Vinyl aromatic compounds are stabilized against undesired polymerization by adding to the vinyl aromatic compounds small amounts of mixtures of alkyl-substituted p-nitrosophenols and p-nitrosophenol.

9 Claims, No Drawings

INHIBITING POLYMERIZATION OF VINYL AROMATIC MONOMERS

FIELD OF THE INVENTION

The present invention relates to the stabilization of ethylenically unsaturated compounds and more particularly to the inhibition of undesired polymerization of vinyl aromatic compounds during storage, shipping or processing.

BACKGROUND

Vinyl aromatic compounds such as styrene undergo undesired spontaneous polymerization (i.e. polymerization of monomers due to heat or the random generation of free radicals in the monomers) during storage, shipping or processing. The problem is particularly acute during purification operations carried out at elevated temperatures, such as distillation. Spontaneous polymerization is disadvantageous not only because it causes fouling of distillation column reboilers and other equipment used for processing vinyl aromatic monomers but also because it usually renders the monomers unfit for use without further treatment. Accordingly, it is desirable and often necessary to inhibit the spontaneous polymerization of vinyl aromatic monomers.

PRIOR ART

To prevent spontaneous polymerization of vinyl aromatic monomers it is common practice to add to the monomers compounds which have polymerization inhibiting activity. A wide variety of such compounds, known as polymerization inhibitors, have been used for this purpose. Sulfur has been widely used in the past to inhibit polymerization of vinyl aromatic compounds, however sulfur usage is undesirable because large quantities of sulfur are required for effective polymerization inhibition. This presents a waste removal problem when the monomer is separated from the sulfur-monomer mixture, which is acccomplished by distillation. The distillation bottoms product, which contains higher molecular weight hydrocarbons, polymer and sulfur, cannot be burned due to the air pollution hazard caused by sulfur oxides. Thus, this material must be disposed of by burial in a waste dump.

In recent times, many chemical compounds have been developed as substitutes for sulfur in polymerization inhibiting applications. These compounds have been used as polymerization inhibitors for vinyl aromatic monomers with varying degrees of success. British Pat. No. 1,064,845 discloses the use of p-nitrosophenol as a polymerization inhibitor for styrene. U.S. Pat. No. 4,237,326 discloses the use of one or more methylated p-nitrosophenol compounds as polymerization inhibitors for styrene. U.S. Pat. No. 2,867,672, issued to Hemmerich, discloses the use of nitrosophenol or 4-nitroso-2-methyl phenol to inhibit the polymerization of sytrene. U.S. Pat. No. 2,361,538, issued to Frang, discloses the use of p-aminophenols to inhibit the polymerization of aromatic olefins. Japanese patent publication No. 49/066687 discloses the use of various compounds, including nitrosophenols as polymerization inhibitors for styrene. West German Pat. No. DD204702A discloses the inhibition of styrene by p-nitrosophenol or its homologues generated in situ. British Pat. No. 2,056,481 discloses the use of p-nitrosophenol or its methyl derivatives as polymerization inhibitors for styrene. U.S. Pat. No. 3,426,063 discloses the use of N-nitrosoaralkhydroxylamines to inhibit thermal polymerization of ethylenically unsaturated hydrocarbons. U.S. Pat. No. 4,434,307 discloses the use of mixtures of N,N-diarylhydroxylamines and tertiary alkyl catechols or tertiary alkyl hydroquinones to inhibit the polymerization of vinyl aromatic compounds.

It has now been discovered that mixtures of alkyl-substituted p-nitrosophenols and p-nitrosophenol provide outstanding polymerization inhibiting activity for vinyl aromatic monomers. Thus, because of the synergistic effect of these mixtures it is now possible to provide unexpectedly superior polymerization inhibiting protection with the same total equivalent weight of alkyl-substituted p-nitrosophenol and p-nitrosophenol mixtures than is obtained by the use of members of either of these groups of compounds by themselves.

Accordingly, it is object of the invention to present stable compositions of vinyl aromatic monomers. It is another object of the invention to present a method of effectively and economically inhibiting spontaneous polymerization of styrene and other vinyl aromatic monomers. These and other objects of the invention are set forth in the following description and examples of the invention.

SUMMARY OF THE INVENTION

According to the invention the protection of vinyl aromatic monomers against spontaneous polymerization is accomplished by incorporating into the monomers mixtures of one or more alkyl-substituted p-nitrosophenols, each alkyl group of which preferably has 1 to 8 carbon atoms, and p-nitrosophenol.

DETAILED DESCRIPTION OF THE INVENTION

The term vinyl aromatic monomer as used in this description includes any of the readily polymerizable vinyl aromatic compounds, e.g. styrene, alpha alkyl styrene, such as alpha methyl styrene, ring alkyl-substituted styrene such as p-methyl styrene, diethylenically substituted benzene compounds, such as divinylbenzene, etc. and mixtures thereof.

The alkyl-substituted p-nitrosophenol compounds used in the invention have the structural formula

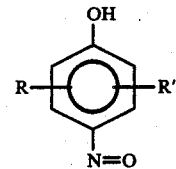

wherein R is hydrogen or a straight- or branched-chain alkyl group having 1 to about 8 and preferably 1 to about 4 carbon atoms and R' is a straight- or branched-chain alkyl group having 1 to about 8 and preferably 1 to about 4 carbon atoms. R and R' may be the same or different alkyl groups. In the most preferred embodiments, R will be hydrogen and R' will be an alkyl group having 1 to about 4 carbon atoms. Although alkyl-substituted p-nitrosophenols having more than about 8 carbon atoms in each alkyl group may be useful in the invention it is desirable that compounds containing 8 or fewer carbon atoms in each alkyl group be used in the invention because the latter compounds are commercially available. Mixtures of two or more alkyl-substituted p-nitrosophenols can also be advantageously used in the compositions of the invention.

Suitable alkyl-substituted p-nitrosophenols include 2-methyl-p-nitrosophenol, 2,6-dimethyl-p-nitrosophenol, 2-t-butyl-p-nitrosophenol, 2,6-di-t-butyl-p-nitrosophenol, 2-isopropyl-p-nitrosophenol, etc. Examples of preferred alkyl-substituted p-nitrosophenols include 2-methyl-p-nitrosophenol and 2-t-butyl-p-nitrosophenol. As noted above, two or more of these compounds may be used in combination, if desired.

Some alkyl-substituted p-nitrosophenols, such as 2-methyl-p-nitrosophenol, are available commercially. Those alkyl-substituted p-nitrosophenols which are not commercially available may be prepared by any of the well known techniques. The preparation of these compounds forms no part of the present invention.

The relative concentrations of alkyl-substituted p-nitrosophenol and p-nitrosophenol used in the invention are generally in the range of about 5 to 95 weight percent alkyl-substituted p-nitrosophenol and 95 to 5 weight percent p-nitrosophenol, based on the total combined weight of these components. In preferred embodiments the concentrations generally fall in the range of about 10 to 90 weight percent alkyl-substituted p-nitrosophenol and 90–10% p-nitrosophenol based on the total combined weight of these components.

The polymerization inhibiting compositions of the invention are well suited for protecting the reboiler sections of a distillation column during distillation of vinyl aromatic monomers because of the high boiling point of these inhibitor compounds. They may be used at temperatures up to about 130° C. or higher at atmospheric pressure. Since the boiling point of various members of the alkyl-substituted p-nitrosophenols are different, compounds which have the desired boiling point can be easily selected from this class. To make up for the inhibitor which is left behind during distillation, additional inhibitor can be added to the vinyl aromatic monomer after it is distilled from heavier hydrocarbons. In some cases it may be desirable to use lower boiling polymerization inhibitors in combination with the inhibitor compositions of the invention. For example, when distilling a vinyl aromatic monomer from higher boiling hydrocarbons it may be advantageous to add a polymerization inhibitor which has a boiling point near or lower than the boiling point of the vinyl aromatic compound. This will provide protection to the overhead portion of the column. It may also be desirable to add with the polymerization inhibitor compositions of the invention other agents, such as corrosion inhibitors, to provide additional protection to process equipment.

The polymerization inhibitor compositions of the invention can be introduced into the monomer to be protected by any conventional method. It is generally introduced just upstream of the point of desired application by any suitable means, such as by the use of a proportionating pump. The polymerization inhibitor composition may be added as a concentrate but it is preferable to add it as a solution which is compatible with the monomer being treated. Suitable solvents include kerosene, naphtha, the lower alkanes such as hexane, aromatic solvents, such as toluene, alcohols, polyols or ketone, etc. It is often preferable to dissolve the inhibitors of the invention in the monomer to which the inhibitor is being added to avoid introducing additional impurities to the monomer. The concentration of polymerization inhibitor is the solvent is desirably in the range of about 1 to 50 weight percent and preferably about 5 to 30 weight percent based on the total weight of inhibitor and solvent.

The polymerization inhibitor is used at a concentration which is effective to provide the desired protection against spontaneous polymerization. It has been determined that amounts of polymerization inhibitor in the range of about 0.5 to 1000 ppm based on the weight of the monomer being treated affords ample protection against undesired polymerization. For most applications the inhibitor is used in amounts in the range of about 5 to 500 ppm.

The polymerization inhibiting composition can be easily removed from the vinyl aromatic monomer prior to polymerization by caustic washing. Such procedures are well known and commonly practiced to separate phenolic type inhibitors from monomers.

The following examples will serve to further illustrate the invention. Unless otherwise stated, parts and percentages are on a weight basis. In the examples styrene, which is representative of vinyl aromatic monomers, was used as the test monomer.

EXAMPLE I (Control)

To a 250 ml three neck flask equipped with a stirrer, a thermometer, a Dean-Stark trap and a water-cooled condenser is charged 200 mls of styrene monomer. The monomer, while being maintained under a vacuum of 23.5 to 26 inches of Hg was heated to and maintained at a temperature in the range of 102° to 105° C. Total reflux was maintained for a period of fifteen minutes after which 100 ml of monomer was removed from the flask in several distillation cuts taken over a two hour period. The reactor contents was then cooled and a 10 ml sample of the reactor residue was drawn and tested to determine the amount of styrene polymer formed by the following procedure: a 10 ml sample of styrene monomer was introduced into 100 ml of cold methanol to quench the polymerization reaction; the methanol-monomer mixture was heated sufficiently to coagulate the polymer formed; and the polymer was recovered from the methanol by filtration, dried overnight at a temperature of 100° F. and weighed. The percentage of polymer formed was determined and reported in the Table in the Run 1 row.

EXAMPLE II (Comparative)

The procedure and test of Example I were repeated except that 25 ppm of para-nitrosophenol was added to the flask just prior to heating. The styrene monomer was tested for polymer formation as indicated in Example I. The results are tabulated in the Table in the Run 2 row.

EXAMPLE III (Comparative)

The procedure and test of Example II were repeated except that 25 ppm of 2-methyl-p-nitrosophenol was substituted for the p-nitrosophenol. The results are tabulated in the Table in the Run 3 row.

EXAMPLE IV

The procedure and test of Example II were repeated except that 20 ppm of 2-methyl-p-nitrosophenol and 5 ppm of p-nitrosophenol were substituted for the p-nitrosophenol. The results are tabulated in the Table in the Run 4 row.

TABLE

| RUN | INHIBITOR | INHIBITOR CONC. ppm | WEIGHT % POLYMER FORMED |
|---|---|---|---|
| 1 | none | — | 10.3 |
| 2 | p-nitrosophenol | 25 | 0.981 |
| 3 | 2-methyl-p-nitrosophenol | 25 | 0.890 |
| 4 | 2-methyl-p-nitrosophenol/p-nitrosophenol (80:20) | 25 | 0.142 |

The benefit of the use of the polymerization inhibitor compositions of the invention is shown in the Table. In the Table the uninhibited monomer contained 10.30 percent polymer after two hours the two hour analysis of the Run 2 and Run 3 samples, which each contained one of the components of the inhibitor system of the invention, showed polymer concentrations of 0.981% and 0.892% respectively; the two hour analysis of the Run 4 sample, which contained the inhibitor composition of the invention, showed a polymer concentration of 0.142. Thus, the inhibitor system of the invention used at 25 ppm shows a greater than six-fold improvement over the use of the next most effective inhibitor, 2-methyl-p-nitrosophenol at the same concentration.

Although the invention is described with particular reference to specific examples, it is understood that the invention includes obvious variants. For example, alkyl-substituted p-nitrosophenols other than 2-methyl-p-nitrosophenol can be used in the invention and the inhibitor system can be formulated to contain more than one member from each of the two specified classes of compounds. The scope of the invention is limited only by the breadth of the appended claims.

What is claimed is:

1. A composition comprised of (a) a vinyl aromatic compound containing an amount effective to inhibit polymerization of said vinyl aromatic compound of a mixture of (1) about 5 to 95 parts by weight of at least one alkyl-substituted p-nitrosophenol, and (2) about 95 to 5 parts by weight of p-nitrosophenol.

2. The composition of claim 1 wherein the total concentration of said mixture of alkyl-substituted p-nitrosophenol and p-nitrosophenol in said composition is 0.5 to 1000 ppm, based on the total weight of vinyl aromatic compound.

3. The composition of claim 1 wherein the vinyl aromatic compound is styrene or alkyl substituted styrene, each alkyl group in (1) has 1 to 8 carbon atoms, the relative concentrations of the compounds in (1) and (2) are 10 to 90 parts by weight and 90 to 10 parts by weight respectively and the total concentration of said mixture of alkyl-substituted p-nitrosophenol and p-nitrosophenol is said composition is 5 to 500 ppm, based on the total weight of vinyl aromatic compound.

4. The composition of claim 3 wherein the vinyl aromatic compound is styrene and the compound in (1) is 2-methyl-p-nitrosophenol.

5. In a method of inhibiting polymerization of a vinyl aromatic compound comprising adding to the vinyl aromatic compound an amount of an polymerization inhibiting agent effective to substantially reduce the rate of polymerization, the improvement comprising using as the agent a combination of:
   (a) about 5 to 95 parts of at least one alkyl-substituted p-nitrosophenol, and
   (b) about 95 to 5 parts of p-nitrosophenol per 100 total parts by weight of the compounds in (a) and (b).

6. The improved method of claim 5 wherein said agent is added to the vinyl aromatic compound in a concentration of about 0.5 to 1000 ppm based on the weight of said vinyl aromatic compound.

7. The improved method of claim 5 wherein each alkyl group of the compound in (a) has 1 to 8 carbon atoms, and said agent is added to the vinyl aromatic monomer in a concentration of about 5 to 500 ppm, based on the weight of said vinyl aromatic compound.

8. The improved method of claim 7 wherein the compound in (a) is 2-methyl-p-nitrosophenol and the compound in (b) is p-nitrosophenol.

9. The improved method of claim 5, 6, 7 or 8 wherein the compounds in (a) and (b) are present in amounts of about 10 to 90 parts and 90 to 10 parts by weight, respectively.

* * * * *